United States Patent [19]
Brack et al.

[11] 3,959,310
[45] May 25, 1976

[54] CATIONIC DYESTUFFS
[75] Inventors: Alfred Brack, Odenthal; Ernst Schmitt, Cologne, both of Germany
[73] Assignee: Bayer Aktiengesellschaft, Leverkusen, Germany
[22] Filed: Jan. 19, 1973
[21] Appl. No.: 324,925

[30] Foreign Application Priority Data
Jan. 19, 1972 Germany............................ 2202316

[52] U.S. Cl.......................... 260/326.9; 260/240 F; 260/247.1 L; 260/256.5 R; 260/268 BC; 260/293.61; 260/310 D; 260/326.11 R; 260/326.12 R; 260/326.62; 260/37 P; 260/286 Q; 260/304 R
[51] Int. Cl.²...................................... C07D 209/56

[58] Field of Search............ 260/326.9, 326.12, 306, 260/307 D, 240 F, 256.5 R, 268 BC, 286, 247.1 L, 293.61, 304, 310 P, 326.11 R, 326.62, 326.9

[56] References Cited
UNITED STATES PATENTS
3,687,972  8/1972  Padmanathan .............. 260/326.9 X Primary Examiner—R. Gallagher
Attorney, Agent, or Firm—Plumley & Tyner

[57] ABSTRACT

Cationic dyestuffs and processes for their manufacture and their use for dyeing, printing and bulk dyeing of natural and synthetic materials, particularly of polyacrylonitrile and copolymers of acrylonitrile with other vinyl compounds, acid modified aromatic polyesters and acid modified polyamides.

9 Claims, No Drawings

CATIONIC DYESTUFFS

The subject of the invention are new cationic dyestuffs of the general formula

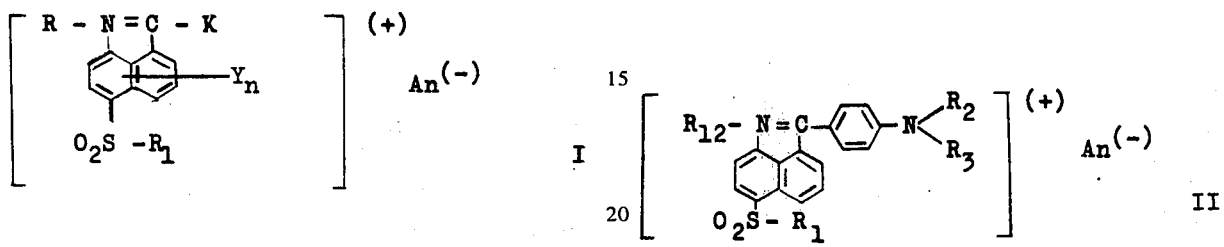

wherein
- R denotes hydrogen, an alkyl, cycloalkyl, aralkyl or aryl radical or an alkylene radical bonded to the naphthalene ring in the o-position,
- $R_1$ denotes an alkyl, cycloalkyl, aralkyl or aryl radical or a saturated or unsaturated heterocyclic radical bonded via carbon,
- Y denotes hydrogen or a non-ionic substituent and/or a carboxyl group,
- n denotes the numbers 1 or 2,
- K denotes the groupings

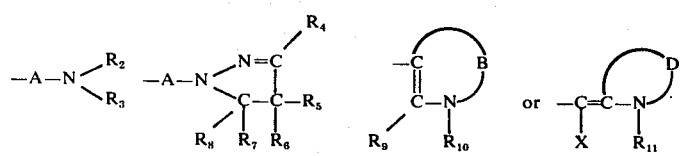

wherein
- A represents an aromatic ring to which further rings can be fused,
- $R_2$ represents hydrogen or an alkyl, cycloalkyl, aralkyl or aryl radical,
- $R_3$ represents an alkyl, cycloalkyl, aralkyl or aryl radical,
- $R_4$ represents an alkyl, cycloakyl, aralkyl, aryl, hydroxyl, alkoxy, carboxylic acid ester, carboxylic acid amide or nitrile group, or a heterocyclic radical,
- $R_5$, $R_6$, $R_7$ and $R_8$ independently of one another represent hydrogen or a radical bonded via carbon,
- $R_9$ represents hydrogen or an alkyl, cycloalkyl aralkyl, aryl, alkoxy or carboxylic acid ester group or a heterocyclic radical,
- $R_{10}$ represents hydrogen or an alkyl, cycloalkyl, aralkyl or aryl radical,
- $R_{11}$ represents an alkyl radical,
- X represents a nitrile, carboxylic acid ester or carboxylic acid amide group,
- B and D independently of one another represent the remaining members of a 5-membered or 6-membered nitrogen-containing ring, and wherein
- $R_2$ can be bonded to $R_3$ or to A by a direct bond or by a hetero-atom, and
- $An^{(-)}$ denotes an anion.

A further subject of the invention are processes for the manufacture of the new dyestuffs and their use for dyeing, printing and bulk dyeing of synthetic, partially synthetic and natural materials.

Preferred dyestuffs are those of the general formula

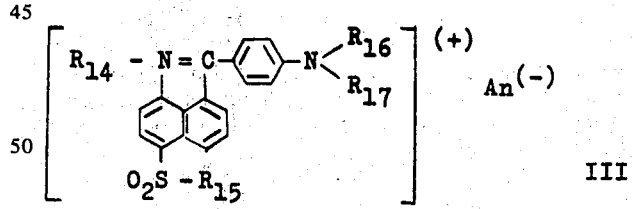

wherein
- $R_1$, $R_2$, $R_3$ and $An^{(-)}$ have the indicated meaning and
- $R_{12}$ denotes an alkyl radical with 1 to 6 C atoms.

Particularly preferred dyestuffs correspond to the general formula $$\left[ R_{14} - N = C - \text{Ar} - N \begin{matrix} R_{16} \\ R_{17} \end{matrix} \right]^{(+)} An^{(-)} \quad \text{III}$$

wherein
- $R_{14}$ denotes methyl, ethyl, propyl, butyl, (meth)allyl or propargyl,
- $R_{15}$ denotes methyl, ethyl, propyl, butyl, pentyl, hexyl, (meth)allyl, propargyl, phenyl or benzyl,
- $R_{16}$ and $R_{17}$ independently of one another denote methyl, ethyl, propyl, butyl, pentyl, hexyl, (meth)allyl or propargyl and
- $An^{(-)}$ denotes an anion.

Amongst these dyestuffs, those of the formulae

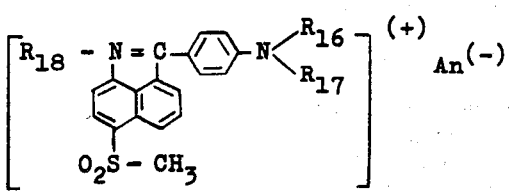

IV and

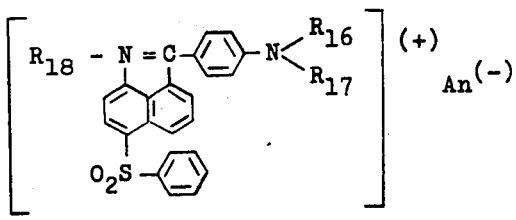

V wherein $R_{16}$, $R_{17}$ and $An^{(-)}$ have the indicated meaning and
$R_{18}$ denotes a methyl or ethyl group
should be singled out particularly.

Possible anionic radicals $An^-$ are the organic and inorganic anions customary for cationic dyestuffs.

Inorganic anions are, for example, fluoride, chloride, bromide and iodide, perchlorate, hydroxyl, radicals of S-containing acids, such as bisulphate, sulphate, disulphate and aminosulphate; radicals of nitrogen-oxygen acids, such as nitrate; radicals of oxygen acids of phosphorus, such as dihydrogen phosphate, hydrogen phosphate, phosphate and meta-phosphate; radicals of carbonic acid, such as bicarbonate and carbonate; further anions of oxygen acids and complex acids, such as methosulphate, ethosulphate, hexafluosilicate, cyanate, thiocyanate, ferrocyanide, ferricyanide, trichlorozincate and tetrachlorozincate, tribromozincate and tetrabromozincate, stannate, borate, divanadate, tetravanadate, molybdate, tungstate, chromate, bichromate and tetrafluoborate, as well an anions of esters of boric acid, such as of the glycerine ester of boric acid, and of esters of phosphoric acid, such as of methyl phosphate.

Organic anions are, for example, anions of saturated or unsaturated aliphatic, cycloaliphatic, aromatic and heterocyclic carboxylic acids and sulphonic acid, such as radicals of acetic acid, chloroacetic acid, cyanoacetic acid, hydroxyacetic acid, aminoacetic acid, methylaminoacetic acid, aminoethylsulphonic acid, methylaminoethylsulphonic acid, propionic acid, n-butyric acid, i-butyric acid, 2-methylbutyric acid, 2-ethyl-butyric acid, dichloroacetic acid, trichloroacetic acid, trifluoroacetic acid, 2-chloropropionic acid, 3-chloropropionic acid, 2-chlorobutyric acid, 2-hydroxypropionic acid, 3-hydroxypropionic acid, 0-ethylglycollic acid, thioglycollic acid, glyceric acid, malic acid, dodecyltetraethylene-glycol-ether-propionic acid, 3-(nonyloxy)-propionic acid, 3-(isotridecyloxy)-propionic acid, 3-(isotridecyloxy)-diethylene-glycol-ether-propionic acid, the ether-propionic acid of an alcohol mixtur with 6 to 10 carbon atoms, thioacetic acid, 6-benzoylamino-2-chloro-caproic acid, nonylphenol-tetraethylene-glycol-ether-propionic acid, nonylphenol-diethylene-glycol-ether-propionic acid, dodecyltetraethylene-glycol-ether-propionic acid, phenoxyacetic acid, nonylphenoxyacetic acid, n-valeric acid, i-valeric acid, 2,2,2-trimethylacetic acid, n-caproic acid, 2-ethyl-n-caproic acid, stearic acid, oleic acid, ricinoleic acid, palmitic acid, n-pelargonic acid, lauric acid, a mixture of aliphatic carboxylic acids with 9 to 11 carbon atoms (Versatic Acid 911 of SHELL), a mixture of aliphatic carboxylic acids with 15 to 19 carbon atoms (Versatic Acid 1519 of SHELL), of coconut fatty acid first runnings, of undecanecarboxylic acid, n-tridecanecarboxylic acid and of a coconut fatty acid mixture; of acrylic acid, methacrylic acid, crotonic acid, proparglyic acid, oxalic acid, malonic acid, succinic acid, glutaric acid, adipic acid, pimelic acid, suberic acid, azelaic acid, the isomer mixture of 2,2,4- and 2,4,4-trimethyladipic acid, sebacic acid, isosebacic acid (isomer mixture), tartaric acid, citric acid, glyoxylic acid, dimethyl-ether-$\alpha,\alpha'$-dicarboxylic acid, methyl-bis-thioglycollic acid, dimethyl-sulphide-$\alpha,\alpha$-dicarboxylic acid, 2,2'-dithio-di-n-propionic acid, fumaric acid, maleic acid, itaconic acid, ethylene-bis-iminoacetic acid, nitrilosulphonic acid, methanesulphonic acid, ethanesulphonic acid, chloromethanesulphonic acid, 2-chloroethanesulphonic acid and 2-hydroxyethanesulphonic acid, and Mersolat, that is to say $C_8$-$C_{15}$-paraffinsulphonic acid, obtained by chlorosulphonation of paraffin oil.

Suitable anions of cycloaliphatic carboxylic acids are, for example, the anions of cyclohexanecarboxylic acid and cyclohexene-3-carboxylic acid and anions of araliphatic monocarboxylic acids are, for example, anions of phenylacetic acid, 4-methylphenylacetic acid and mandelic acid.

Examples of suitable anions of aromatic carboxylic acids are the anions of benzoic acid, 2-methylbenzoic acid, 3-methylbenzoic acid, 4-methylbenzoic acid, 4-tert.-butylbenzoic acid, 2-bromobenzoic acid, 2-chlorobenzoic acid, 3-chlorobenzoic acid, 4-chlorobenzoic acid, 2,4-dichlorobenzoic acid, 2,5-dichlorobenzoic acid, 2-nitrobenzoic acid, 3-nitrobenzoic acid, 4-nitrobenzoic acid, 2-chloro-4-nitrobenzoic acid, 6-chloro-3-nitrobenzoic acid, 2,4-dinitrobenzoic acid, 3,4-dinitrobenzoic acid, 3,5-dinitrobenzoic acid, 2-hydroxybenzoic acid, 3-hydroxybenzoic acid, 4-hydroxybenzoic acid, 2-mercaptobenzoic acid, 4-nitro-3-methylbenzoic acid, 4-aminobenzoic acid, 5-nitro-2-hydroxybenzoic acid, 3-nitro-2-hydroxybenzoic acid, 4-methoxybenzoic acid, 3-nitro-4-methoxybenzoic acid, 4-chloro-3-hydroxybenzoic acid, 3-chloro-4-hydroxybenzoic acid, 5-chloro-2-hydroxy-3-methylbenzoic acid, 4-ethylmercapto-2-chlorobenzoic acid, 2-hydroxy-3-methylbenzoic acid, 6-hydroxy-3-methylbenzoic acid, 2-hydroxy-4-methylbenzoic acid, 6-hydroxy-2,4-dimethylbenzoic acid, 6-hydroxy-3-tert.-butylbenzoic acid, phthalic acid, tetrachlorophthalic acid, 4-hydroxphthalic acid, 4-methoxyphthalic acid, isophthalic acid, 4-chloroisophthalic acid, 5-nitroisophthalic acid, terephthalic acid, nitroterephthalic acid, and diphenyl-3,4-carboxylic acid, o-vanillic acid, 3-sulphobenzoic acid, benzene-1,2,4,5-tetracarboxylic acid, naphthalene-1,4,5,8-tetracarboxylic acid, biphenyl-4-carboxylic acid, abietic acid, phthalic acid mono-n-butyl ester, terephthalic acid monomethyl ester, 3-hydroxy-5,6,7,8-tetrahydronaphthalene-2-carboxylic acid, 2-hydroxy-1-naphthoic acid and anthraquinone-2-carboxylic acid.

Suitable anions of heterocyclic carboxylic acids are, for example, the anions of pyromucic acid, dehydromucic acid and indolyl-3-acetic acid.

Suitable anions of aromatic sulphonic acids are, for example, the anions of benzenesulphonic acid, benzene-1,3-disulphonic acid, 4-chlorobenzenesulphonic acid, 3-nitrobenzenesulphonic acid, 6-chloro-3-nitrobenzenesulphonic acid, toluene-4-sulphonic acid, toluene-2-sulphonic acid, toluene-ω-sulphonic acid, 2-chlorotoluene-4-sulphonic acid, 1-hydroxybenzenesulphonic acid, n-dodecylbenzenesulphonic acid, 1,2,3,4-tetrahydronaphthalene-6-sulphonic acid, naphthalene-1-sulphonic acid, naphthalene-1,4- or -1,5-disulphonic acid, naphthalene-1,3,5-trisulphonic acid, 1-naphthol-2-sulphonic acid, 5-nitronaphthalene-2-sulphonic acid, 8-aminonaphthalene-1-sulphonic acid, stilbene-2,2′-disulphonic acid and biphenyl-2-sulphonic acid.

A suitable anion of heterocyclic sulphonic acids is, for example, the anion of quinoline-5-sulphonic acid.

Further possibilities are the anions of arylsulphinic, arylphosphonic and arylphosphonous acids, such as benzenesulphinic and benzenephosphonic acid.

Colourless anions are preferred. For dyeing from an aqueous medium, anions which do not excessively impair the solubility of the dyestuff in water are preferred. For dyeing from organic solvents, anions which assist the solubility of the dyestuff in organic solvents or at least do not influence it adversely, are frequently also preferred.

The anion is in general determined by the manufacturing process and by the purification of the crude dyestuff which may be carried out. In general, the dyestuffs are in the form of halides (especially as chlorides or bromides) or as methosulphates, ethosulphates, sulphates, benzenesulphonates or toluenesulphonates or as acetates. The anions can be replaced by other anions in a known manner.

By an alkyl radical there is understood a saturated or unsaturated aliphatic radical with, preferably, 1 to 6 C atoms, which can contain non-ionic substituents and/or carboxyl groups, for example the methyl, ethyl, n- and iso-propyl, n-, iso- and tert. butyl and the various isomeric pentyl and hexyl radicals as well as the vinyl, propenyl, allyl and propargyl radical or the hydroxyethyl, chloroethyl or cyanoethyl radical.

By cycloalkyl radicals there are meant, for example, cyclopentyl and cyclohexyl radicals, which can be substituted by non-ionic radicals and/or carboxyl groups.

Aryl radicals are, for example, phenyl radicals which optionally have non-ionic substituents and/or are substituted by carboxyl groups, and their ring-fusion products, such as the naphthalene radical optionally substituted by non-ionic substituents and/or by carboxyl groups.

Heteryl radicals are, for exaple, 5- or 6-membered heterocyclic rings, such as the thienyl, pyridyl, pyrrolyl, indolyl-2, indolyl-3, benzothiazolyl-2 or benzoxazolyl-2 radical and their derivatives substituted by non-ionic radicals or by carboxyl groups.

Aralkyl radicals are, for example, alkyl radicals substituted by aryl or heteryl radicals.

Non-ionic substituents in the sense of the present invention are the non-ionising substituents which are customary in dyestuff chemistry, such as fluorine, chlorine or bromine; alkyl radicals, especially straight-chain or branched alkyl radicals with 1 – 6 C atoms; aralkyl radicals; alkenyl radicals; aryl radicals; alkoxy radicals, especially alkoxy radicals with 1 – 4 C atoms; aralkoxy radicals; aryloxy radicals an alkylthio radicals, preferably alkylthio radicals with 1 – 3 C atoms; aralkylthio radicals; arylthio radicals; nitro; nitrile; alkoxycarbonyl, preferably those with an alkoxy radical with 1 – 4 C atoms; the formyl radical; alkylcarbonyl radicals, especially those with an alkyl group with 1 – 4 C atoms; arylcarbonyl; aralkylcarbonyl radicals; alkoxycarbonyloxy radicals, preferably with an alkyl group with 1 – 4 C atoms; alkylcarbonylamino radicals, preferably with an alkyl group with 1 – 4 C atoms, and arylcarbonylamino radicals; alkylsulphonylamino radicals, preferably with an alkyl group with 1 – 3 C atoms; arylsulphonylamino groups; ureido; N-aryl- or N-alkyl-ureido, aryloxycarbonylamino and alkyloxycarbonylamino; carbamoyl; N-alkyl-carbamoyl; N,N-dialkylcarbamoyl; N-alkyl-N-aryl-carbamoyl, sulphamoyl; N-alkylsulphamoyl; N-N-dialkyl-sulphamoyl; alkylsulphonyl; alkenylsulphonyl; aralkylsulphonyl, 1 – 4 C atoms preferably being present in the alkyl radicals mentioned; arylsulphonyl, carboxylic acid alkyl ester, carboxylic acid aryl ester, sulphonic acid alkyl ester and sulphonic acid aryl ester groups.

The new dyestuffs are obtained in a manner which is in itself known by condensation of 4-sulphonyl-1,8-naphtholactams of the general formula

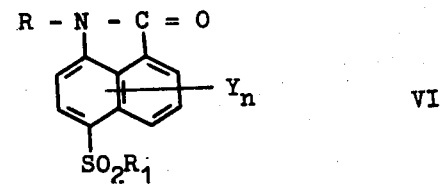

wherein
R, $R_1$, Y and n have the indicated meaning with compounds of the general formula

especially with compounds of the general formulae

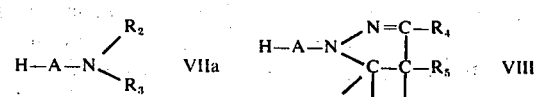

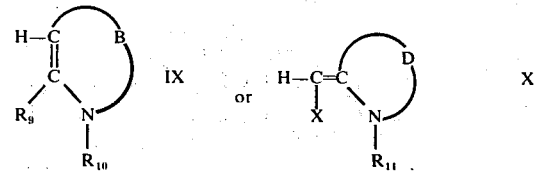

wherein

A, B, K, D, X and $R_2$ to $R_{11}$ have the indicated meaning, whilst using a condensation agent which yields an anion $An^{(-)}$, such as phosphorus oxychloride, phosphorus trichloride and phosphorus pentachloride, tin tetrachloride and titanium tetrachloride, with or without addition of other agents which cause water to split off, such as phosphorus pentoxide, aluminium chloride or zinc chloride, and, if desired, subsequent conversion of those dyestuffs I, in which R represents hydrogen, into the corresponding colour bases of the formula

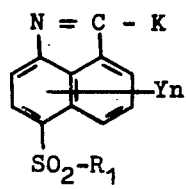

XI and their treatment with quaternising agents.

Suitable 4-sulphonyl-naphtholactams are, for example, N-methyl-, N-ethyl-, N-n-propyl-, N-iso-propyl-, N-n-butyl-, N-iso-butyl-, N-cyclohexyl-, N-benzyl-, N-(o-, m- or p-) methylbenzyl-, N-β-phenylethyl-, N-phenyl-, N-p-tolyl- and N,2-trimethylene-4-methysulphonyl-1,8-naphtholactam, the corresponding 4-ethyl-, 4-n-propyl-, 4-iso-propyl- and 4-n-butylsulphonyl derivatives, 4-methyl-, 4-ethyl-, 4-phenyl-, 4-o-, m- or p-tolylsulphonyl-1,8-naphtholactam, N-methyl-, N-ethyl-, N-β-chloroethyl-, N-β-cyanoethyl-, N-β-methoxyethyl- and N-β-methoxycarbonylethyl-4-phenylsulphonyl-1,8-naphtholactam, the corresponding 4-benzyl- and 4-o-, m- or p-methylbenzylsulphonyl derivatives, N-methyl- and N-ethyl-4-β-chloroethyl-, -β-cyanoethyl- and -β-hydroxyethylsulphonyl-1,8-naphtholactam and 2-ethyl-4-methylsulphonyl-1,8-naphtholactam.

The sulphonyl-naphtholactams can easily be manufactured according to known processes, for example by oxidation of the corresponding mercapto compounds of the formula

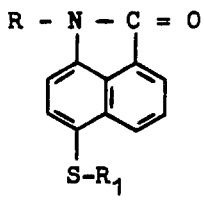

XII or by alkylation (or aralkylation or the like) of the corresponding sulphinic acids, which in turn are available through reduction of the sulphochlorides, or especially advantageously by introduction of the $-SO_2R_1$ radical by the Friedel-Crafts method, either directly from the naphtholactams which are unsubstituted in the 4-position and sulphochlorides or from naphtholactam-4-sulphochlorides and suitable compounds which are accessible to the Friedel-Crafts reaction such as aromatic hydrocarbons and their sufficiently reactive substitution products and reactive heterocyclic compounds.

Suitable amines of the formula VIIa are, for example, N,N-dimethyl-, -diethyl-, -di-n-propyl-, -di-n-butyl-, -di-β-hydroxyethyl-, -di-β-chloroethyl-, -di-β-cyanoethyl- and -di-β-ethoxyethyl-aniline, -m-toluidine and -m-anisidine, N-methyl-N-iso-amyl-, N-methyl-N-n-hexyl-, N-ethyl-N-β-chloroethyl-, N-ethyl-N-β-methoxycarbonylethyl- and N-ethyl-N-allyl-aniline, N-ethyl-, N-benzyl-, N-iso-butyl-, N,N-dimethyl-, N,N-diethyl-, N-methyl-N-β-cyanoethyl- and N-iso-propyl-aminohydroquinone-dimethyl- und -diethyl-ether, 3-methoxycarbonylamino-N,N-diethylaniline, diphenylamine, N-methyl-, N-ethyl- and N-allyl-diphenyl-amine, cyclohexylaniline, N-methyl- and N-β-cyanoethyl-tetrahydroquinoline, N-phenyl-morpholine, -piperidine and -pyrrolidine, N-ethyl-N-β-dimethylaminoethylaniline and 7-ethyl-2-methyl-indoline.

Suitable pyrazolines of the formula VIII are, for example, 1-phenyl-3-methyl-, 1-phenyl-3-hydroxy-, 1,3-diphenyl-, 1-phenyl-3-(4'-methoxyphenyl-, 1-phenyl-3-(4'-methylphenyl)-, 1-phenyl-3-(4'-phenoxyphenyl)-, 1-phenyl-3-(α- or β-naphthyl)-, 1-phenyl-3-styryl-, 1,5-diphenyl-3-styryl-, 1-phenyl-3-(α-thienyl)-, 1-α-naphthyl-3-(4'-methoxyphenyl)- and 1-α-naphthyl-3-(α-thienyl)-pyrazoline-Δ².

Suitable heterocyclic compounds of the formula IX are, for example, 1,2,5-trimethylpyrrole, 1-phenyl-2,5-dimethyl-pyrrole, indole, 2-D-methyl- and 2-phenyl-indole, 2-methyl-7-ethyl-indole, 1,2-dimethyl-indole, 1-methyl-2-phenylindole, 1-methyl-2-phenyl-5-methoxy-indole, 1-methyl-2-α-thienyl-indole, 1-methyl-2-methoxy-indole and 1-methyl-indole-2-carboxylic acid methyl ester.

Suitable heterocyclic compounds of the formula X are, for example, 1,3,3-trimethyl-2-cyanomethylene-indoline, its 5-methoxy-, 5-ethoxy-, 5-n-butoxy-, 5-methyl-, 5-ethyl-, 5-chloro-, 5-cyano-, 5-methoxy-carbonyl-, 5-acetylamino-, 5-methylsulphonyl-, 7-ethyl-, 7-ethoxy-, 7-chloro-, 5-methoxy-7-chloro- and 4,7-dimethoxy- derivative, 1-ethyl-3,3-dimethyl-2-cyanomethylene-indoline, 1,3,3-trimethyl-2-methoxycarbonyl-methylene-indoline, 1,3,3-trimethyl-2-phenylamidocarbonyl-methylene-indoline, 1,3,6-trimethyl-4-cyanomethylene-pyrimidone, 2-cyanomethylene-3-methylbenzthiazoline and its 5-methoxy-, 6-methoxy-, 5,6-dimethoxy- and 5,6diethoxy-derivative.

The new dyestuffs are suitable for dyeing, printing and bulk dyeing materials which consist wholly or predominantly of polymerised unsaturated nitriles such as acrylonitrile and vinylidene cyanide or of acid-modified polyesters of acid-modified polyamides. They are furthermore suitable for the remaining known applications of cationic dyestuffs, such as dyeing and printing cellulose acetate, coir, jute, sisal and silk, of tannin-treated cotton and paper, for the manufacture of ball pen pastes and rubber stamp inks and for use in flexographic printing. The dyeings and prints on the first-mentioned materials, especially on polyacrylonitrile, are distinguished by their very high fastness level, above all their very good fastness to light, wet processing, rubbing, decatising, sublimation and perspiration.

As compared to previously known similar dyestuffs, the new dyestuffs are distinguished by improved fastness properties, especially improved fastness to light, and by a desirable bathochromic displacement of the colour shade. The dyeings and prints manufactured with the dyestuffs show to a particular extent the desired property of little or no change in their colour shade in artificial light, that is to say they have a good "evening colour". Further advantages reside in the unusual clarity of the colour shade, which is particularly important for the manufacture of brilliant prints, in their uniform absorption on the abovementioned materials, above all on polyacrylonitrile, and in the ease of combination with commercially available dyestuffs.

The parts mentioned in the examples are parts by weight.

EXAMPLE 1

55 parts of N-ethyl-4-methylsulphonyl-1,8-naphtholactam are stirred with 35 parts of N,N-diethyl-aniline in 400 parts of phosphorus oxychloride, with addition of 30 parts of phosphorus pentoxide, for 8 to 10 hours at 80 to 85°C. The cooled mixture is poured into 2,000 to 3,000 parts of ice water. As soon as the excess phosphorus oxychloride has hydrolysed, 300 parts of concentrated sodium hydroxide solution are added with cooling, maximally at 35°C. Hereupon, the dyestuff of the formula

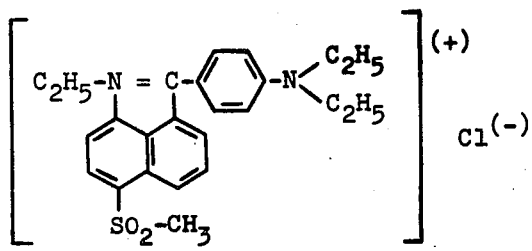

separates out in a form which is already largely pure. After stirring for several hours the dyestuff if filtered off and washed with dilute sodium chloride solution. The yield is approximately quantitative. If desired, the dyestuff can be purified by recrystallisation from water. It gives very fast and brilliant blue dyeings and prints on polyacrylonitrile.

The naphtholactam derivative used was manufactured as follows:

N-Ethylnaphtholactam-4-sulphinic acid 30 g of N-ethylnaphtholactam-4-sulphonic acid chloride were added, with stirring, to 300 ml of 10% strength sodium carbonate solution, and 30 g of Na dithionite were then added over the course of 10 minutes. The reaction mixture is stirred for 2 hours at 60°C, left to cool and acidified with 5% strength HCl. The product which has precipitated is filtered off, washed with water and dried.

Yield: 25.6 g.

The resulting crude yellow product is purified by again stirring it with 10% strength NaOH. After filtering off insoluble constituents, the sulphinic acid is precipitated from the filtrate by means of 5% strength hydrochloric acid, dried and recrystallised from alcohol.

Yield: 19 g; melting point: 112°–116°C.

4-Methylsulphonyl-N-ethylnaphtholactam 26.1 g of N-ethylnaphtholactam-4-sulphinic acid are suspended in 100 ml of water. 6.5 g of potassium hydroxide are added, the mixture is warmed to 40°C and after adding 20 ml of alcohol, 13 g of dimethylsulphate are added dropwise over the course of 1½ hours. The pH is kept at above 7 – 8 by adding aqueous potassium hydroxide solution (a total of 6.6 g of potassium hydroxide in approximately 10% strength solution). Simultaneously with the last half of the potassium hydroxide solution, a further 7 g of dimethyl sulphate are added over the course of 45 minutes. The reaction mixture is stirred for a further 3 hours at 40°C and rendered alkaline with 10% strength aqueous sodium hydroxide solution, the product is filtered off and the yellow crystalline mass is washed with water and dried.

Yield: 11.5 g; melting point, after recrystallisation from dimethylformamide/alcohol: 198°–202°C (sintering from 194°C onwards).

If instead of the diethylaniline N-methyl-, N-ethyl-, N-β-chloroethyl- or N-β-cyanoethyl-tetrahydroquinoline or one of the following amines is used, in each case in equivalent amount, very fast dyestuffs are again obtained.

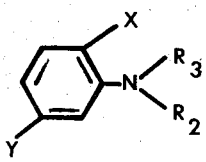

| $R_2$ | $R_3$ | X | Y | Colour Shade on Polyacrylonitrile |
|---|---|---|---|---|
| Methyl | Methyl | Hydrogen | Hydrogen | strongly reddish-tinged blue |
| Hydrogen | iso-Butyl | Hydrogen | Hydrogen | blue-violet |
| Hydrogen | Benzyl | Ethoxy | Ethoxy | blue |
| Hydrogen | p-Methyl-benzyl | Methoxy | Methoxy | blue |
| Hydrogen | Ethyl | Methoxy | Methoxy | greenish-tinged blue |
| β-Cyanoethyl | Ethyl | Methoxy | Methoxy | greenish-tinged blue |
| β-Chloroethyl | Ethyl | Hydrogen | Hydrogen | reddish-tinged blue |
| n-Propyl | n-Propyl | Hydrogen | Hydrogen | blue |
| n-Butyl | n-Butyl | Hydrogen | Hydrogen | blue |
| n-Butyl | β-Chloroethyl | Hydrogen | Methyl | blue |
| Ethyl | Ethyl | Hydrogen | Methoxy | blue |
| Ethyl | Ethyl | Hydrogen | Chlorine | blue |
| Ethyl | Ethyl | Hydrogen | Methoxycarbonylamino | greenish-tinged blue |
| Ethyl | Ethyl | Hydrogen | Dimethylamidocarbonylamino | greenish-tinged blue |
| Ethyl | β-Methoxycarbonylethyl | Hydrogen | Hydrogen | reddish-tinged blue |
| Cyclohexyl | Methyl | Hydrogen | Hydrogen | blue |

-continued

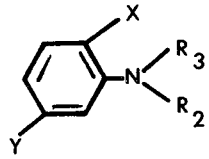

| $R_2$ | $R_3$ | X | Y | Colour Shade on Polyacrylonitrile |
|---|---|---|---|---|
| Phenyl | Methyl | Hydrogen | Hydrogen | blue |
| o-Tolyl | Methyl | Hydrogen | Hydrogen | reddish-tinged blue |
| o-Methoxy-phenyl | Methyl | Hydrogen | Hydrogen | blue |
| Ethyl | β-Dimethylaminoethyl | Hydrogen | Hydrogen | reddish-tinged blue |
| Ethyl | β-Methoxyethyl | Hydrogen | Hydrogen | blue |
| Ethyl | β-Cyanoethyl | Hydrogen | Hydrogen | reddish-tinged blue |
| Ethyl | β-Carbonamidoethyl | Hydrogen | Hydrogen | reddish-tinged blue |
| Ethyl | β-Phenylethyl | Hydrogen | Hydrogen | reddish-tinged blue |
| $R_2+R_3$ = | Morpholine | Hydrogen | Hydrogen | reddish-tinged blue |
| $R_2+R_3$ = | Piperidine | Hydrogen | Hydrogen | blue |
| $R_2+R_3$ = | Pyrrolidine | Hydrogen | Hydrogen | blue |
| $R_2+R_3$ = | N-β-Cyanoethyl-piperazine | Hydrogen | Hydrogen | blue |

EXAMPLE 2

35.1 parts of N-ethyl-4-p-tolylsulphonyl-1,8-naphtholactam and 15 to 30 parts of N,N-diethylaniline are stirred with 350 to 450 parts of phosphorus oxychloride and 15 to 30 parts of phosphorus pentoxide for 15 to 20 hours at 90°C. The cooled mixture is poured into 3,500 parts of water. The dyestuff immediately separates out in a crystalline form, in almost quantitative yield. It corresponds to the formula

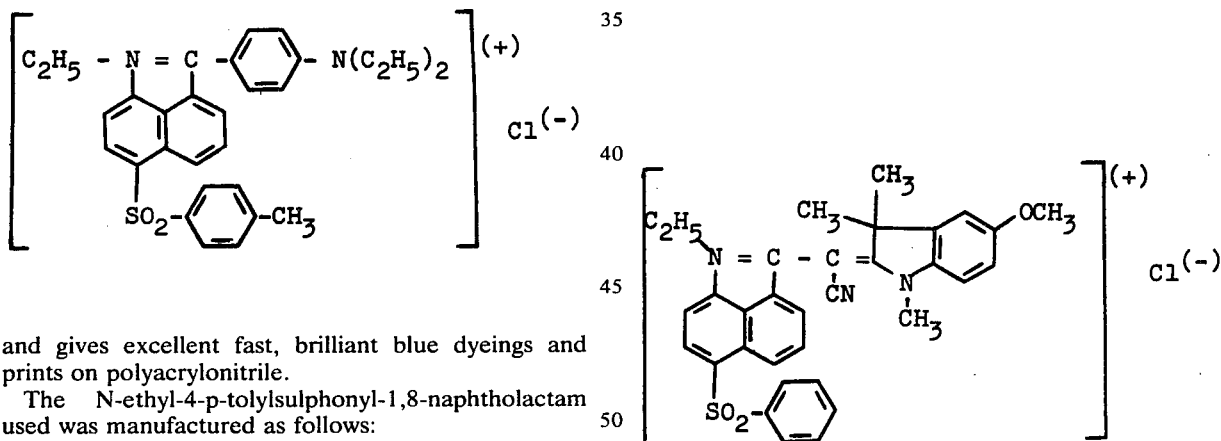

and gives excellent fast, brilliant blue dyeings and prints on polyacrylonitrile.

The N-ethyl-4-p-tolylsulphonyl-1,8-naphtholactam used was manufactured as follows:

28 g of $AlCl_3$ were added, whilst stirring and excluding moisture, to a mixture of 40 g of N-ethylnaphtholactam, 88 g of p-toluenesulphochloride and 60 ml of nitrobenzene, and thereafter the whole is warmed to 60°C. At this temperature, a further 56 g of $AlCl_3$ are added in portions, in the course of which the temperature rises to 100°C. The mixture is stirred for 5 hours at 110° to 130°C and then poured out onto ice and the product is filtered off and washed with cyclohexane and ligroine.

Yield: 72.5 g; melting point: 200°–202°C.

Analogous N-alkyl-4-p-toluenesulphonyl-naphtholactams are obtained by reaction of toluenesulphochloride with N-methyl-, N-n-propyl-, N-iso-propyl-, N-n-butyl- and N-β-cyanoethyl-1,8-naphtholactam. Following the procedure of Example 2 these lactam derivatives give very similar dyestuffs of corresponding structure.

EXAMPLE 3

33.7 parts of N-ethyl-4-phenylsulphonyl-1,8-naphtholactam and 23.0 parts of 1,3,3-trimethyl-5-methoxy-2-cyanomethylene-indoline in 75 parts of chlorobenzene are stirred with 25 parts of phosphorus oxychloride for 6 hours at 80° to 90°C. After cooling, the mixture is diluted with 75 to 100 parts of benzene. The dyestuff which has separated out is purified by recrystallisation from water with addition of active charcoal. It corresponds to the formula and dyes polyacrylonitrile violet, with excellent fastness properties.

The phenylsulphonylnaphtholactam had been manufactured in accordance with the process described in Example 2, using benzenesulphochloride. It melts at 160° to 162°C.

If instead of the indicated 2-cyanomethylene-indoline the particular equivalent amount of one of the following heterocyclic methylene bases is used, very fast, new dyestuffs are again obtained. The color shade on polyacrylonitrile is indicated in brackets: 1,3,3-trimethyl-2-cyanomethylene-indoline (red-violet), 1-ethyl-3,3-dimethyl-5-ethoxy-2-cyanomethylene-indoline (blue-violet), 1,3,3-trimethyl-5-chloro-2-cyanomethylene-indoline (violet), 1,3,3-trimethyl-7-methoxy-2-cyanomethylene-indoline (blue-violet), 1,3-dimethyl-4-cyanomethylene-pyrimidone-(2) (reddish-tinged blue), 1,3,6-trimethyl-4-cyanomethylene-pyrimidone-(2) (reddish-tinged blue), 3-methyl-2cyanomethylene-benzthiazoline (reddish-tinged blue), 3-ethyl-2-cyanomethylene-6-methoxy-benzthiazoline (blue) and 3-n-butyl-2-cyanomethylene-benzthiazoline (reddish-tinged blue).

EXAMPLE 4

68 parts of 4-(p-tolylsulphonyl)-1,8-naphtholactam and 40 parts of N-methyldiphenylamine are heated with 300 parts of phosphorus oxychloride to about 100°C for 20 hours. After cooling, the excess phosphorus oxychloride is hydrolysed by introducing the mixture into ice water and the strongly acid suspension is adjusted to pH = 1 to 2 with concentrated sodium hydroxide solution. The dyestuff of the formula

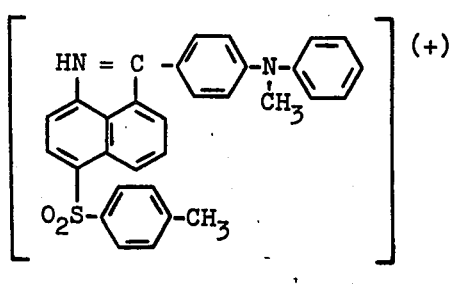

which has separated out crystalline and in practically quantitative yield, is filtered off. On dissolving it in approx. 800 parts of alcohol, adding alcoholic sodium hydroxide solution or potassium hydroxide solution in slight excess and precipitating with 500 to 1,000 parts of water, the dyestuff base of the formula

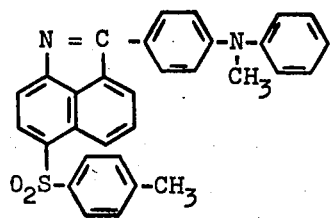

is obtained. This dyestuff base melts at 212° to 216°C as the crude product and at 220°C after recrystallization from toluene.

Analogously, when using diethylaniline the dyestuff base of the formula

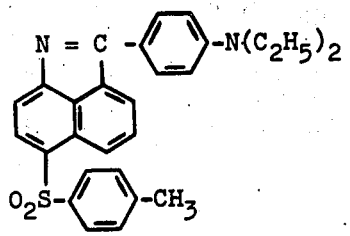

is obtained, which after recrystallisation from toluene melts at about 200°C.

20 parts of one of these dyestuff bases are heated with about a ten-fold amount of β-chloroethyl alcohol (= ethylene chlorohydrin) for 8 hours under reflux. The dyestuff of the formula

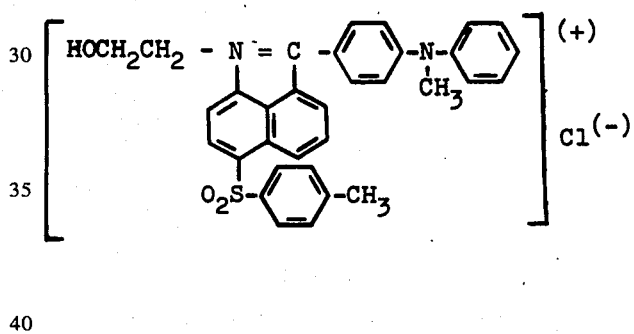

or

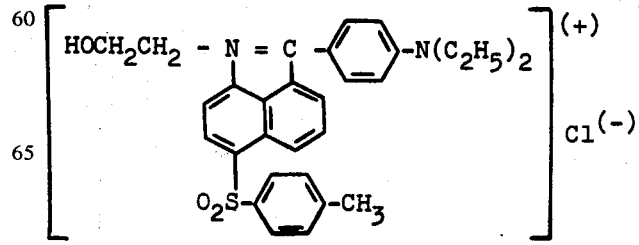

is produced. The dyestuff is isolated in the usual manner by diluting the solution with water and salting-out. The dyestuff with N-methyl-diphenylamine gives extremely light-fast blue dyeings and prints and the dyestuff with diethylaniline gives reddish-tinged blue dyeings and prints.

4-(p-Tolylsulphonyl)-1,8-naphtholactam was manufactured from naphtholactam in accordance with the process described in Example 2; it melts at 297° to 299°C.

is obtained in the form of the double salt with zinc chloride.

The condensation can also be carried out without addition of zinc chloride if the dyestuff is to be obtained free of zinc.

The naphtholactam derivative used was manufactured analogously to the isomeric p-tolyl derivative and melts at 196° to 199°C.

If instead of N-ethyl-N-β-dimethylamino-ethylaniline one of the following amines is used, and the analogous procedure is followed, very fast dyestuffs are again obtained:

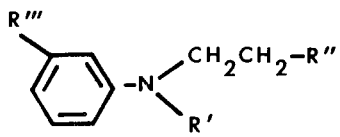

| R' | R'' | R''' | Colour Shade on Polyacrylonitrile |
|---|---|---|---|
| Methyl | Diethylamine | Hydrogen | reddish-tinged blue |
| n-Butyl | Diethylamine | Hydrogen | blue |
| Ethyl | Piperidyl | Hydrogen | blue |
| Ethyl | Pyrrolidinyl | Hydrogen | blue |
| Ethyl | Morpholinyl | Hydrogen | blue |
| Ethyl | Dimethylamino | Methyl | blue |
| Ethyl | Dimethylamino | Methoxy | greenish-tinged blue |
| Ethyl | Dimethylamino | Ethoxy | greenish-tinged blue |
| Ethyl | Dimethylamino | Chlorine | greenish-tinged blue |
| n-Butyl | β-Chloroethyl | Hydrogen | reddish-tinged blue |
| Ethyl | β-Ethoxyethyl | Hydrogen | reddish-tinged blue |
| Ethyl | β-Cyanoethyl | Ethoxy | blue |
| Ethyl | β-Hydroxy-carbonylethyl | Hydrogen | reddish-tinged blue |
| Ethyl | Hydrogen | Methoxycarbonylamino | blue |
| Ethyl | Hydrogen | Methylamidocarbonylamino | blue |
| Ethyl | Hydrogen | Hydroxy | blue |

EXAMPLE 5

35.1 parts of N-ethyl-4-o-tolylsulphonyl-1,8-naphtholactam, 20 parts of N-ethyl-N-β-dimethylamino-ethyl-aniline and 100 parts of phosphorus oxychloride, with the addition of 15 parts of anhydrous zinc chloride, was warmed to 95°C for 8 to 10 hours. The mixture is worked-up Example accordance with the instructions of Example 2. The blue dyestuff of the formula

EXAMPLE 6

37.2 parts of 4-(p-chlorophenyl)-sulphonyl-N-ethyl-1,8-naphtholactam and 13.5 parts of 2-methyl-indole are warmed with 200 parts of phosphorus oxychloride. At about 90°C, the mixture turns deep blue-violet. It is stirred for 4 to 5 hours at 100°C and allowed to cool, and the excess phosphorus oxychloride is decomposed by stirring with a ten-fold amount of water. The dyestuff of the formula

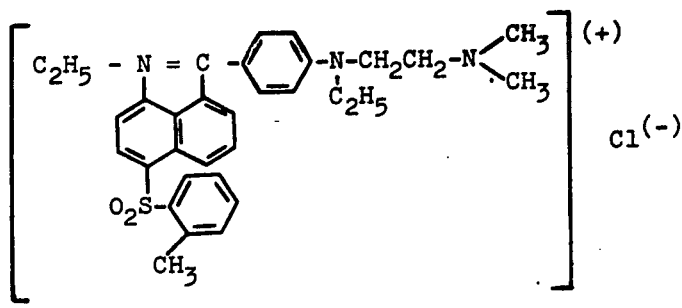

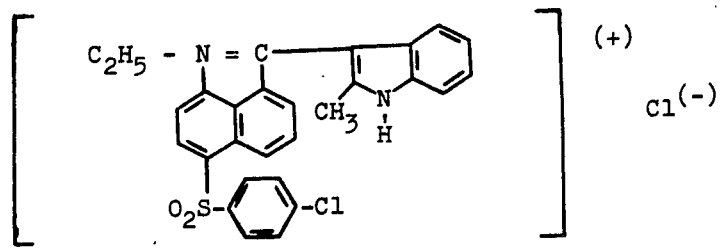

precipitates in a crystalline form. It can be recrystallised from water and dyes polyacrylonitrile blue-violet, with excellent fastness properties.

The naphtholactam derivative used was manufactured in accordance with the instructions in Example 2, using 4-chlorobenzenesulphochloride, and melts at 144° to 147°C.

EXAMPLE 7

317 parts of 4-n-butylsulphonyl-N-ethyl-1,8-naphtholactam and 207 parts of 1-methyl-2-phenyl-indole are heated with 1,250 parts of phosphorus oxychloride for 8 hours to about 100°C. The mixture is cooled and poured into 10,000 parts of ice water. The dyestuff which separates out can be purified in the usual manner by recrystallisation from water. It corresponds to the formula bromobutane are added dropwise at 50°C over the course of 1/2 hour. The mixture is then stirred for 1 hour at 70°C and 1 hour at 100°C. For working-up, 250 ml of water and 70 ml of 20% strength aqueous sodium hydroxide solution are added, the mixture is stirred for 1 hour at room temperature, whilst keeping the pH at above 10 by adding additional sodium hydroxide solution, and the crystalline yellow mass is then filtered off.

Yield: 40 g; melting point, after recrystallisation from glacial acetic acid: 139° to 145°C.

EXAMPLE 8

4 parts of N-ethyl-4-(3'-nitrophenylsulphonyl)-1,8-naphtholactam are stirred with 2.4 parts of N,N-diethylaniline, 4 parts of phosphorus oxychloride and 1.2 parts of anhydrous zinc chloride initially at 70° – 90°C and then for 15 – 20 hours at 100° – 110°C. The reaction mixture is poured out into ice/water and the dyestuff which precipitates is recrystallised from water. The dyestuff of the formula

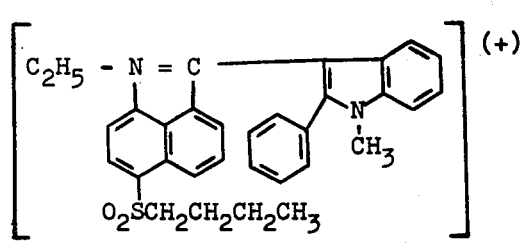

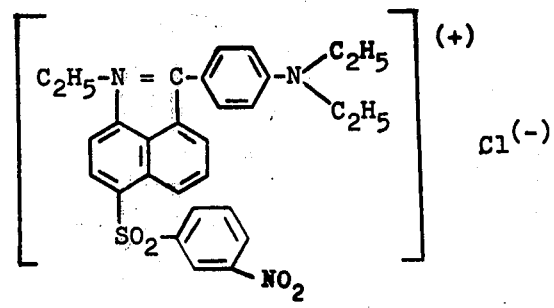

and gives blue dyeings and prints of excellent fastness on polyacrylonitrile.

The butylsulphonyl-naphtholactam was manufactured as follows:

12 g of powdered potassium hydroxide were introduced into a solution of 50 g of N-ethylnaphtholactam-4-sulphinic acid in 100 ml of dimethylformamide. When all the material has dissolved, 35 g of n- is obtained in the form of the double salt with zinc chloride, which dyes polyacrylonitrile in a clear blue shade.

On following the analogous procedure and using the starting products indicated below, the following dyestuffs are obtained in the form of the zinc chloride double salt, which dye polyacrylonitrile fabrics in the indicated shades:

| Dyestuff | Colour Shade |
|---|---|
| 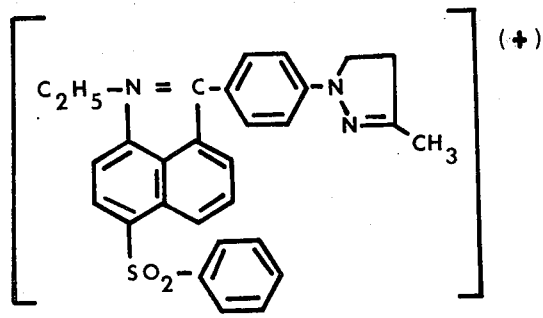 from N-ethyl-4-phenylsulphonyl-1,8-naphtholactam and 1-phenyl-3-methylpyrazoline | blue |

| Dyestuff | Colour Shade |
|---|---|
| 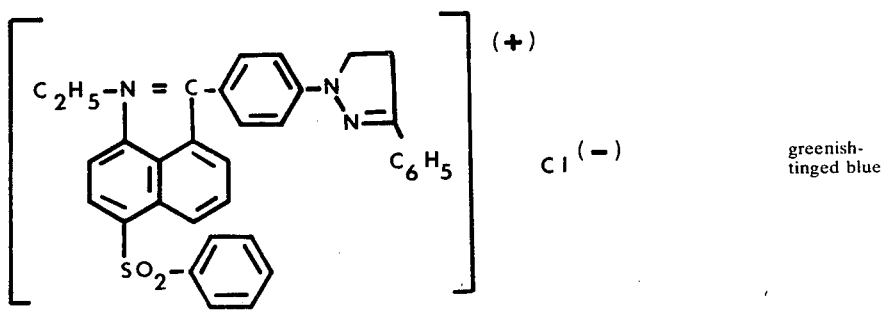 from N-ethyl-4-phenylsulphonyl-1,8-naphtholactam and 1,3-diphenylpyrazoline | greenish-tinged blue |
| 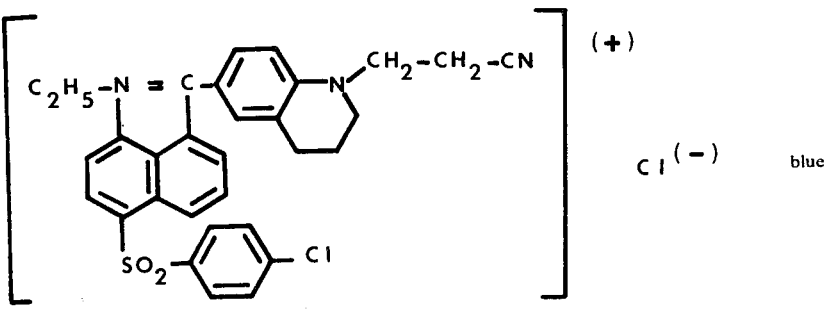 from N-ethyl-4-p-chlorophenylsulphonyl-1,8-naphtholactam and N-cyanoethyltetrahydroquinoline | blue |
| 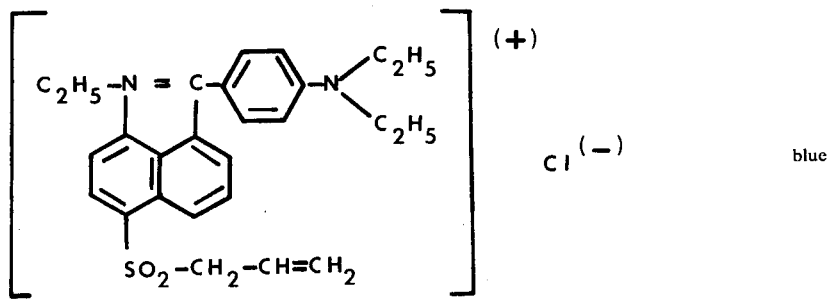 from N-ethyl-4-allylsulphonyl-1,8-naphtholactam and N,N-diethylaniline | blue |
| 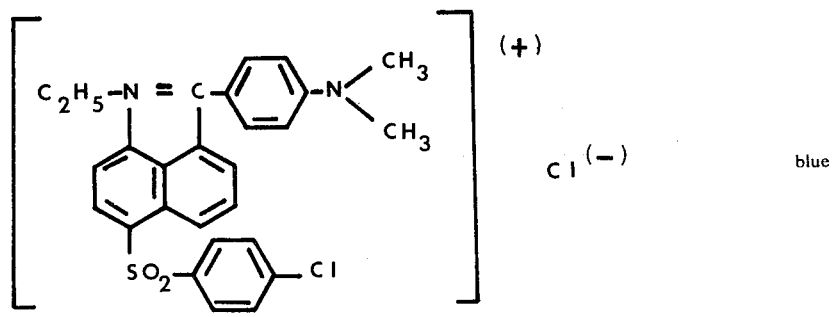 from N-ethyl-4-p-chlorophenylsulphonyl-1,8-naphtholactam and N,N-dimethylaniline | blue |

| Dyestuff | Colour Shade |
|---|---|
| 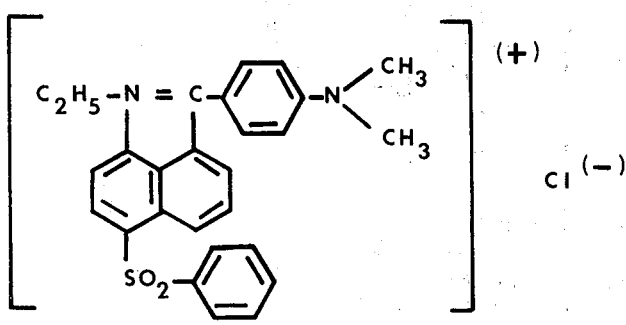<br>from N-ethyl-4-phenylsulphonyl-1,8-naphtholactam and N,N-dimethylaniline | blue |
| 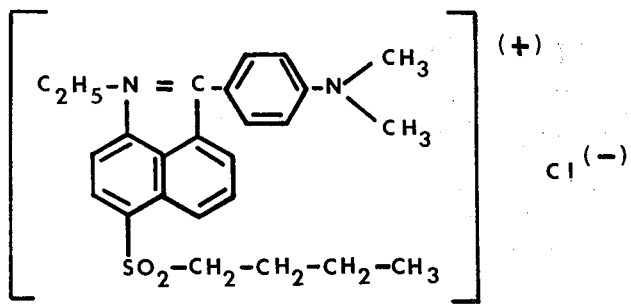<br>from N-ethyl-4-n-butylsulphonyl-1,8-naphtholactam and N,N-dimethylaniline | reddish-tinged blue |
| 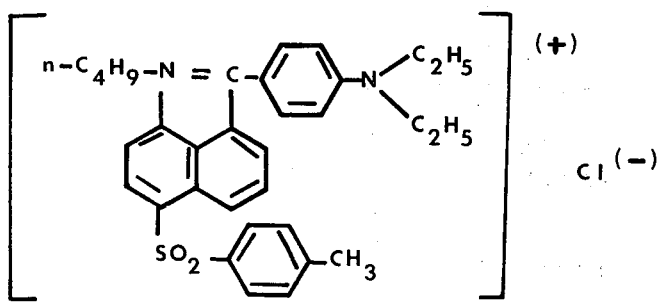<br>from N-n-butyl-4-p-tolylsulphonyl-1,8-naphtholactam and N,N-diethylaniline | blue |

The N-ethyl-4-allylsulphonyl-1,8-naphtholactam used for the 4th. dyestuff of the table is obtained as follows:

12 parts of powdered potassium hydroxide are introduced into a solution of 50 parts of N-ethyl-1,8-naphtholactam-4-sulphinic acid in 95 parts of dimethylformamide. When all the material has dissolved, 30 parts of allyl bromide are added dropwise at 50°C over the course of ½ hour. Thereafter the mixture is stirred for 1 hour at 70°C and 1 hour at 100°C and is allowed to cool, and 250 parts of water together with 86 parts of 20% strength aqueous sodium hydroxide solution are added to the reaction mixture. The mixture is stirred for 1 hour at room temperature, whilst keeping the pH-value above 9 by adding further sodium hydroxide solution if necessary. The mixture is filtered and the residue is recrystallised from glacial acetic acid.

Yield: 30 parts

Melting point after a further recrystallisation from glacial acetic acid: 160° – 164°.

lized from water with addition of charcoal. The dyestuff corresponds to the formula

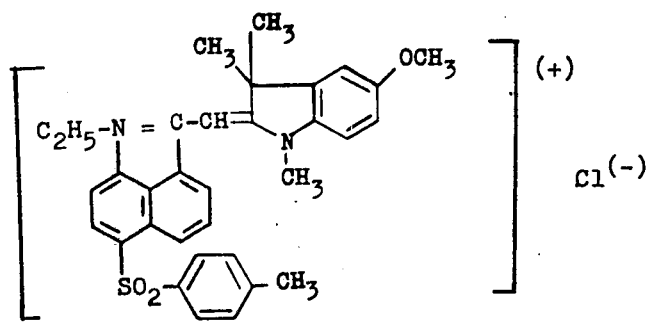

EXAMPLE 9

7.2 parts of N-ethyl-4-p-tolylsulphonyl-1,8-naphtholactam, 8.1 parts of 1,3,3-trimethyl-5-methoxy-2-methyleneindoline, 9 parts of phosphorus oxychloride and 5 parts of phosphorus pentoxide are stirred for 25 hours at 100° – 120°. The dyestuff obtained after pouring out the reaction product into ice/water is recrystallized from water with addition of charcoal and dyes polyacrylonitrile in red-violet shades.

If the method indicated above of condensation with phosphorus oxychloride and phosphorus pentoxide is employed and the starting products indicated below are used, the following dyestuffs are obtained, which dye polyacrylonitrile in the indicated shades:

| Dyestuff | Colour Shade |
|---|---|
| from N-ethyl-4-n-butylsulphonyl-1,8-naphtholactam and 2-phenyl-7-ethylindole. | corinth |
| from N-ethyl-4-n-butylsulphonyl-1,8-naphtholactam and 2-phenylindole | corinth |
| from N-ethyl-4-phenylsulphonyl-1,8-naphtholactam and N-methyl-p-ethoxydiphenylamine | blue |

EXAMPLE 10

3.2 parts of N-ethyl-4-n-butylsulphonyl-1,8-naphtholactam are mixed with 1.7 parts of diphenylamine, 3 parts of phosphorus oxychloride and 3.2 parts of tin tetrachloride and the mixture is then warmed and stirred for 15 minutes at 135°. 20 parts of methanol are added to the reaction mixture whilst still warm and the whole is then cooled by stirring for 1 hour and filtered. The residue is boiled up with water. On cooling, the dyestuff of the formula

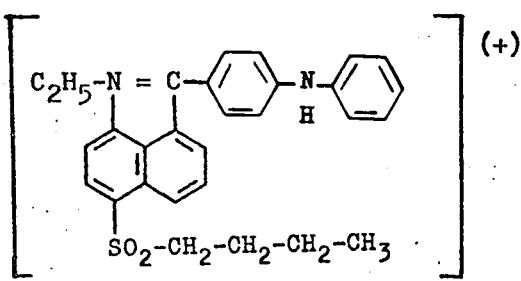

separates out from the filtrate; it dyes polyacrylonitrile in a clear blue shade having very good fastness to light.

EXAMPLE 11

An aqueous dyebath which contains, per liter, 0.75 g of 30% strength acetic acid, 0.40 g of sodium acetate and 0.25 g of the dyestuff of the formula

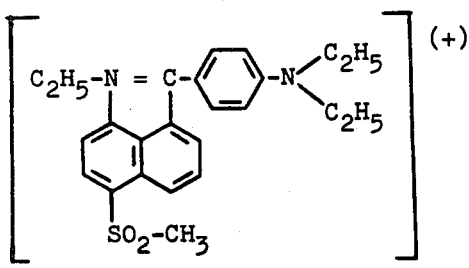

is charged, at approx. 45°C, with the amount of polyacrylonitrile fibres corresponding to a liquor ratio of 1 : 40, heated to the boil over the course of 20 to 30 minutes and kept at this temperature for 30 to 60 minutes. After rinsing and drying the fibre, a brilliant blue dyeing of very good fastness to light is obtained.

EXAMPLE 12

Acid-modified polyglycol terephthalate fibres of the DACRON 64 type (Du Pont), or as described in Belgian Patent Specification 549,179 and in U.S. Pat. No. 2,893,816, are introduced at 20°C, in a liquor ratio of 1 : 40, into an aqueous bath which per liter contains 3 g of sodium sulphate, 0.5 to 2 g of an oleyl-polyglycolether (50 mols of ethylene oxide), 2.5 to 5 g of diphenyl and 0.3 g of the dyestuff of the formula of Example 1, and which was adjusted with acetic acid to a pH-value of 4.5 to 5.5. The bath is heated to 98°C over the course of 30 minutes and kept at this temperature for 60 minutes. Thereafter the fibres are rinsed and dried. A brilliant blue dyeing of very good fastness properties is obtained.

EXAMPLE 13

0.75 g of the dyestuff of the formula of Example 1 are worked into a paste with a 20-fold amount of hot water, with addition of a little acetic acid, in a dyeing beaker of 500 ml capacity located in a heated water bath, and the paste is dissolved in hot water. 0.5 g of the reaction product of 50 mols of ethylene oxide with 1 mol of oleyl alcohol is further added to the dyeing liquor and the whole is made up to 500 ml with cold water. The pH-value of the dyeing liquor is adjusted to 4.5 – 5 with acetic acid or sodium acetate.

10 g of piece goods of acid-modified polyamide are constantly agitated in this dyeing liquor whilst raising the temperature to 100°C for 15 minutes. Dyeing is carried out at the boil for 15 to 20 minutes and the material is rinsed with cold water and subsequently dried, for example by ironing or in a drying cabinet at 60° to 70°C. A material which is dyed blue is obtained.

EXAMPLE 14

A polyacrylonitrile fabric is printed with a printing paste of the following composition:

```
30 parts of the dyestuff of the formula of Example 1
50 parts of thiodiethylene glycol
30 parts of cyclohexanol
30 parts of 30% strength acetic acid
500 parts of crystal gum
30 parts of aqueous zinc nitrate solution (d = 1.5) and
330 parts of water.
```

The resulting print is dried, steamed for 30 minutes and subsequently rinsed. A brilliant blue print having very good fastness properties is obtained.

We claim:
1. Cationic dyestuff of the formula

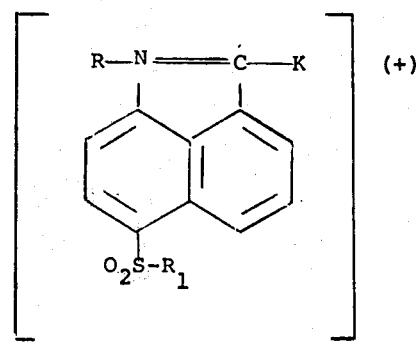

wherein
R is hydrogen, methyl, n-propyl, i-propyl, n-butyl, -cyanoethyl, or -hydroxyethyl;
$R_1$ is methyl, n-butyl, allyl, phenyl, p-tolyl, o-tolyl, p-chlorophenyl, or m-nitrophenyl;
K is

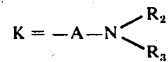

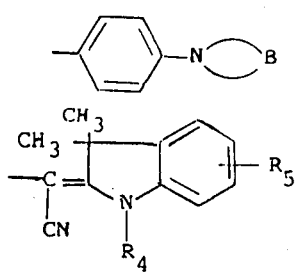

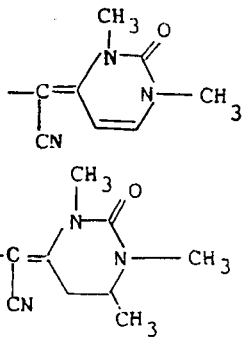

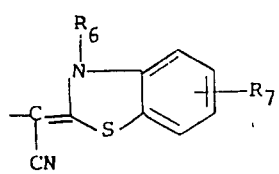

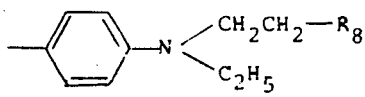

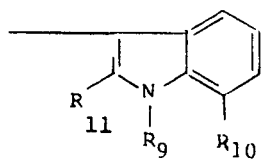

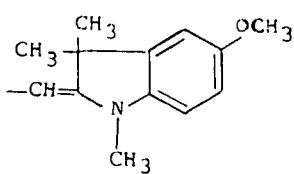

N-methyl-tetrahydroquinolinyl,
N-ethyl-tetrahydroquinolinyl,
N-β-chloroethyl-tetrahydroquinolinyl,
N-β-cyanoethyl-tetrahydroquinolinyl;

A is p-phenylene, 2,5-diethoxy-p-phenylene, 2,5-dimethoxy-p-phenylene 3-methyl-p-phenylene, 3-methoxy-p-phenylene, 3-chloro-p-phenylene, 3-methoxycarbonyl-amino-p-phenylene, 3-dimethylamido-carbonylamino-p-phenylene, 3-ethoxy-p-phenylene, or 3-methylamido-carbonylamino-p-phenylene;

$R_2$ is methyl, ethyl, n-propyl, n-butyl, i-butyl, β-chloroethyl, diethylaminoethyl, cyclohexyl, phenyl, p-othoxyphenyl, o-methoxyphenyl, o-tolyl, benzyl, or p-methylbenzyl;

$R_3$ is hyrogen, methyl, ethyl, n-propyl, or n-butyl;

$R_4$ is methyl or ethyl;

$R_5$ is hydrogen, 5-chloro, 5-methoxy, or 5-ethoxy;

$R_6$ is methyl, ethyl, or n-butyl;

$R_7$ is hydrogen or 6-methoxy;

$R_8$ is chloro, cyano, methoxy, methoxycarbonyl, β-ethoxyethyl, β-cyanoethyl, β-hydroxycarbonylethyl, dimethylamino, carbonamido, phenyl, piperidyl, pyrrolidinyl, or morpholinyl;

$R_9$ is hydrogen or methyl;

$R_{10}$ is hydrogen or ethyl;

$R_{11}$ is methyl or phenyl;

B is the remaining portion of morpholinyl, piperidinyl, pyrrolidinyl, 3-methylpyrazolinyl 3-phenylpyrazolinyl, or N-β-cyanoethylpiperazinyl; and $An^{(-)}$ is an anion.

2. Cationic dyestuffs of the general formula

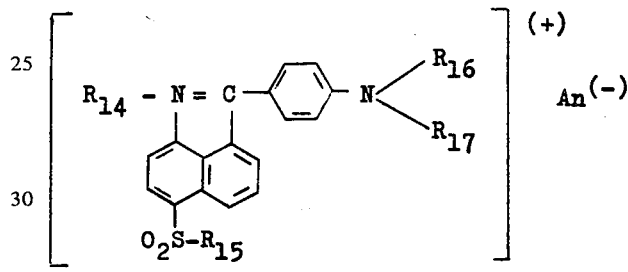

wherein
$R_{14}$ denotes methyl, ethyl, propyl, or butyl,
$R_{15}$ denotes methyl, ethyl, propyl, butyl, pentyl, hexyl, phenyl, or benzyl,
$R_{16}$ and $R_{17}$ independently of one another denote methyl, ethyl, propyl, butyl, pentyl, hexyl, (meth)allyl, or propargyl and
$An^{(-)}$ denotes an anion.

3. Cationic dyestuffs of the general formula

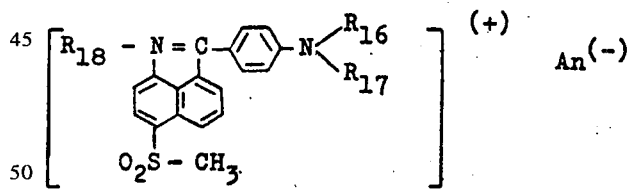

wherein
$R_{16}$ and $R_{17}$ independently of one another denote methyl, ethyl, propyl, butyl, pentyl, hexyl, (methy)allyl or propargyl,
$R_{18}$ denotes a methyl or ethyl group and
$An^{(-)}$ denotes an anion.

4. Cationic dyestuffs of the general formula

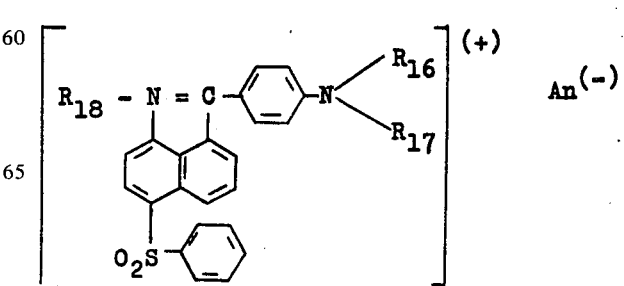

wherein
R₁₆ and R₁₇ independently of one another denote methyl, ethyl, propyl, butyl, pentyl, hexyl, (meth)allyl or propargyl,
R₁₈ denotes a methyl or ethyl group and
An $^{(-)}$ denotes an anion.
5. A cationic dyestuff of the formula
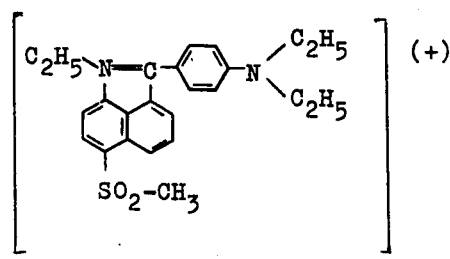
6. A cationic dyestuff of the formula
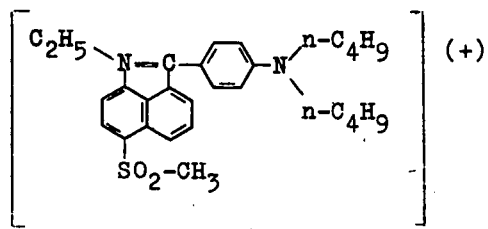
7. A cationic dyestuff of the formula
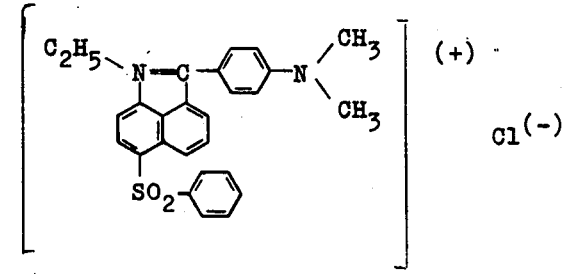
8. A cationic dyestuff of the formula
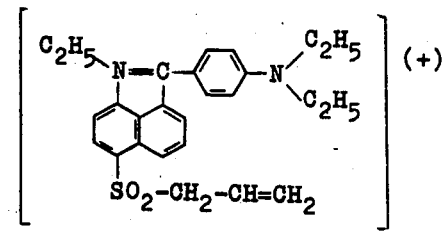
9. A cationic dyestuff of the formula
* * * * *